United States Patent

Sandoz et al.

Patent Number: 5,938,698
Date of Patent: Aug. 17, 1999

[54] KIT SYSTEM FOR CEMENTED PROSTHESES

[75] Inventors: Yvan Sandoz, Winterthur; Alex Seidl, Zürich, both of Switzerland

[73] Assignee: Sulzer Orthopaedie AG, Baar, Switzerland

[21] Appl. No.: 08/900,555

[22] Filed: Jul. 25, 1997

[30] Foreign Application Priority Data

Oct. 7, 1996 [EP] European Pat. Off. .............. 96810672

[51] Int. Cl.⁶ ................ A61F 2/02; A61F 2/28; A61F 2/30; A61F 2/32; A61F 2/38
[52] U.S. Cl. .................. 623/11; 623/16; 623/18; 623/20; 623/22
[58] Field of Search .................. 623/20, 22, 23, 623/16, 18, 11

[56] References Cited

U.S. PATENT DOCUMENTS 4,563,778  1/1986  Roche et al. ............................ 623/16
4,827,919  5/1989  Barbarito .
5,387,241  2/1995  Hayes .
5,658,338  8/1997  Tullos .

FOREIGN PATENT DOCUMENTS 2 259 253   3/1993   United Kingdom .
WO 94/07440  4/1994   WIPO .
WO 95/11640  5/1995   WIPO .

Primary Examiner—David J. Isabella
Assistant Examiner—John M. Black
Attorney, Agent, or Firm—Townsend and Townsend and Crew LLP

[57] ABSTRACT

Areal spacers for prosthesis parts can be cemented into bones and enable a prosthesis part to be cemented in with a correction of the position of its functional surfaces without producing additional risks during the cementing. Since the spacers themselves consist of hardened bone cement, a secure, homogeneous binding with the fluid bone cement arises. At the same time, these spacers also enable a fine kit-like graduation and an exact positioning of prosthesis parts during cementing.

9 Claims, 4 Drawing Sheets

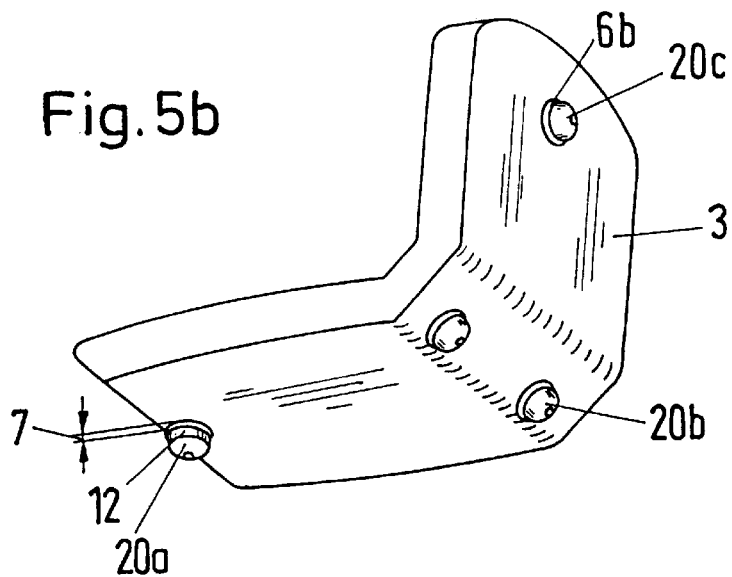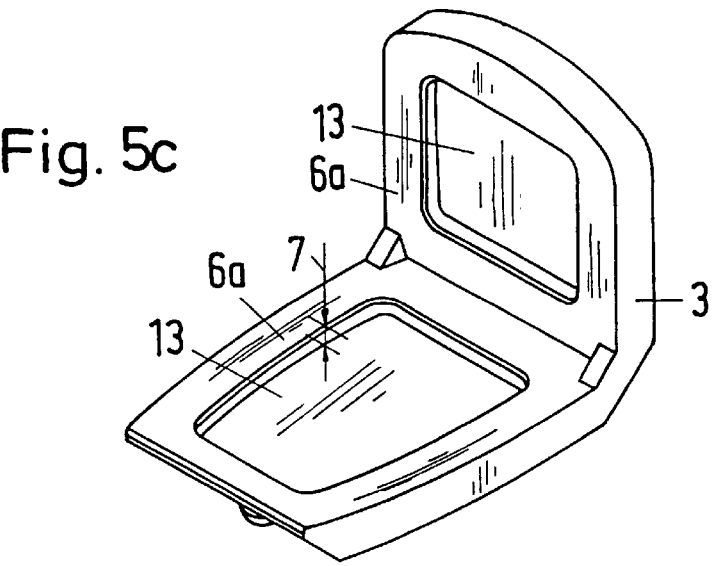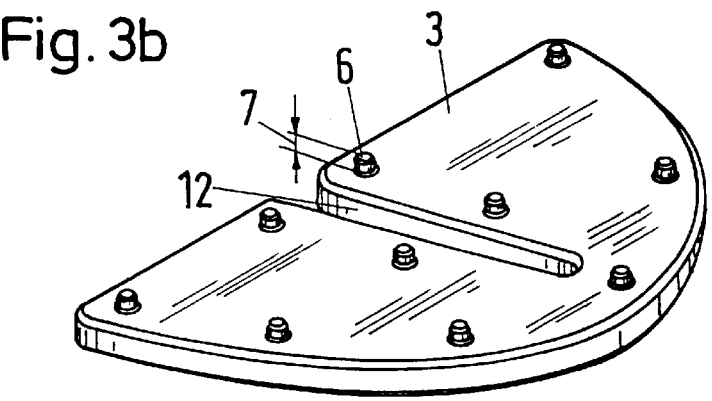

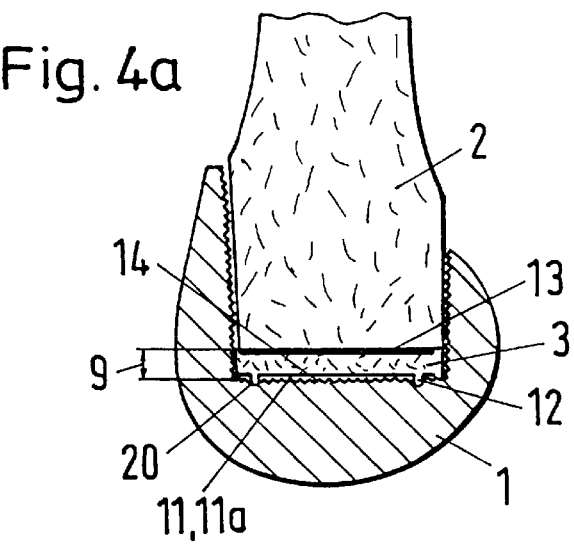
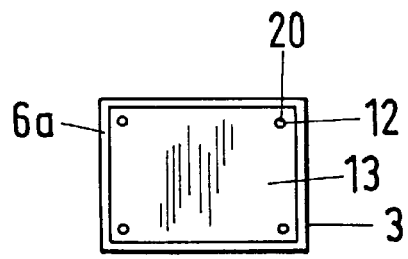
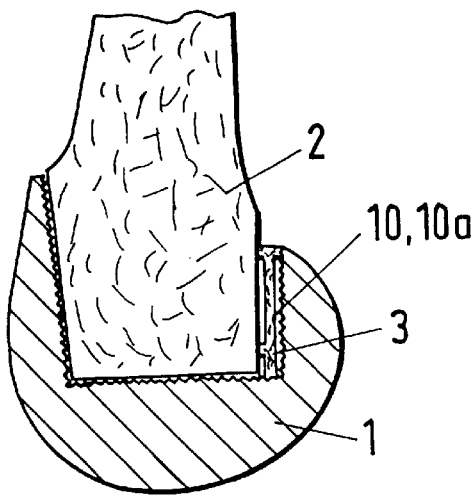
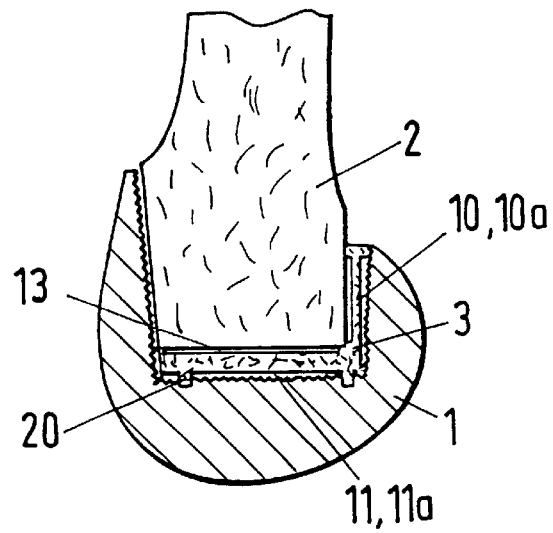

KIT SYSTEM FOR CEMENTED PROSTHESES

BACKGROUND OF THE INVENTION

The invention relates to a kit system for cemented prostheses, in particular for cemented knee prostheses, in which a prosthesis joint part is securable to a resected bone by means of bone cement.

With cemented prosthesis parts, the part is secured to a resected bone with bone cement, with the bone cement flowing into protrusions and recesses in the bones and the prosthesis and, on solidifying, anchoring both parts with respect to one another. In order to position the functional surfaces of prosthesis parts at the right place in spite of differing resections of the bone, different filler pieces have been developed in kit form which can enlarge the distance between the resected surface and the functional surface in steps.

For a metallic tibia platform which can be secured to a tibia by means of bone cement, it is possible to use intermediate plates of different thickness between the platform and the bearing shell. The securing of the bearing shell via an intermediate piece of this kind is however so problematic that many manufacturers prefer to use bearing shells of differing heights.

A further possibility involves in the use of intermediate plates of differing thicknesses which are secured to the underside of the tibia platform by screws and which can be cemented in along with the platform which has been secured to them. Thus the company Smith & Nephew Richards Inc., 1450 Brooks Rd., Memphis, Tenn. 38116, USA developed metallic intermediate plates of differing thickness and with structured surfaces which can be anchored both to the platform and to the bone with bone cement. Such anchorings have the disadvantage that, in addition to the anchoring between the bone cement and the tibia platform, two further anchorings with dovetail-like protrusions and recesses from the intermediate plate to the bone cement are required. Here it depends on the skill of the surgeon whether the bone cement actually flows into the undercuts at the intermediate plate.

SUMMARY OF THE INVENTION

The object of the invention is to provide a kit with a secure connection between the intermediate plate and the bone cement. This object is satisfied, in that the kit of the parts system has at least one prefabricated areal spacer of hardened bone cement which can be secured at its areal faces with bone cement to the bone and the prosthesis part respectively, in order to increase the distance between the prosthesis part and the bone.

Experiments have shown that spacers of this kind, which can be kept in stock in various sizes and thicknesses, completely unite at their surfaces with the bone cement when it is still in the fluid state. Thus, for example, for spacers of PMMA, the surface is re-dissolved by a bone cement of PMMA, which is briefly still wetting in the fluid state, to such an extent that a homogeneous transition in the material arises even for completely smooth surfaces. A spacer of this kind has the advantage that, as far as the security of the fastening of the cemented prostheses is concerned, there is no greater risk than if the prosthesis is cemented in directly. On the contrary, small quantities of cement are sufficient for the securing, the position of the prosthesis can be determined very precisely in advance, and the prosthesis can hardly slide about even when the cement is still in a fluid state. This effect is enhanced further by the structuring of the surface of the spacer, in that protrusions that lie on the opposing face and are possibly centered there, ensure that a uniform and thin cement layer arises. Here the protrusions can be executed as relatively thin bridges or knobs which serve as a path limitation when the prosthesis is pressed into place.

Furthermore, shallow cavities with peripheral edges can be formed, into which the liquid cement can be filled in order to enclose it relative to the opposing surface independently of the direction of gravity and in order to squeeze out excess cement. The position of the prosthesis can thus be varied and checked very precisely by measurement or by test pieces modelled on the spacers prior to the actual cementing. Due to the fact that the variation of the distance of the functional surfaces of the prosthesis from the resected bone has been transferred to a "cheap part" which involves no additional risks, a stock of finely graded thicknesses is possible. Since the constitution of the bone as well as an unavoidable scatter play a role in the resection of a bone, spacers with areal faces inclined with respect to one another in wedge shape can also be of advantage for purposes of compensation in addition to spacers with parallel areal faces. A further advantage results if the spacers can be centered with respect to the prosthesis part via auxiliary surfaces and can thus be pushed on over the prosthesis at the intended position until the bone cement has hardened. Centering can also take place if the spacer and the opposing surface are bent at angles in a plurality of planes or when the areal faces are sections of spherical surfaces.

The manufacture of the spacers from liquid bone cement can be done by casting, by injection or by the warm pressing of semi-fabricates, with the manufacturing process being adapted to the quantity to be produced. Since a chip forming machining of the shape is not necessary, the relatively brittle behavior of bone cement with respect to the alternating stresses arising during chip forming machining can be avoided.

BRIEF DESCRIPTION OF THE DRAWINGS

FIG. 3b is an enlarged schematic view of the spacer of FIG. 3a;

FIG. 4a is a schematic sagittal section of an artificial femur condyle cemented in with a spacer in accordance with the invention for depth correction;

FIG. 4b is a schematic view of a condyle in accordance with FIG. 4a with a spacer for correction in the sagittal direction;

FIG. 4c is a schematic view of a spacer with a peripherally protruding edge for facing the prosthesis;

FIG. 5a is a schematic sagittal section of an artificial femur condyle with an angled spacer;

FIG. 5b is an enlarged schematic lower view of an angled spacer in accordance with FIG. 5a;

FIG. 5c is a schematic upper view of an angled spacer in accordance with FIG. 5b;

DESCRIPTION OF THE PREFERRED EMBODIMENTS

Figure 1:
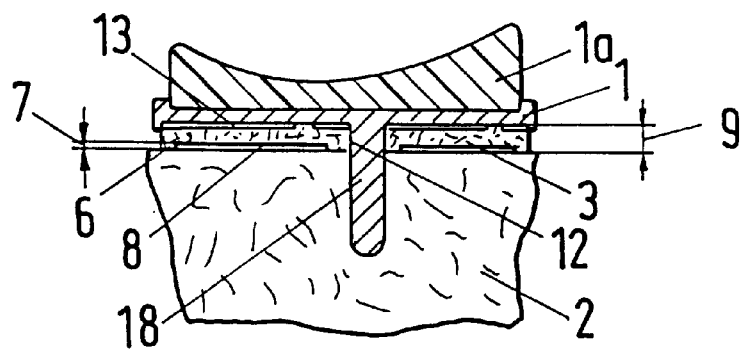
FIG. 1 is a schematic sagittal section through a tibia platform which is connected to a tibia bone via a spacer of bone cement in accordance with the invention.

The Figures show areal spacers for prostheses which can be cemented into bones and enable a prosthesis part to be cemented in with a correction of the position of its functional surfaces without producing additional risks during the cementing. Since the spacers themselves consist of hardened bone cement, a secure, homogeneous bonding to the liquid bone cement arises. At the same time these spacers also enable a fine kit-like graduation and an exact positioning of parts of prostheses during cementing.

FIGS. 1, 2, 3a, 3b show areal spacers 3 of hardened bone cement which can be fastened to a tibia platform 1 and to a resected tibia bone 2 with liquid bone cement. Through a kit-like stocking of areal spacers 3 of different thicknesses 9, the bearing surface of a bearing shell 1a which is anchorable to the tibia platform 1 can be raised. The areal spacer 3 is provided with protrusions 6, 6a which determine the thickness 9 of the spacer 3 and at the same time allow a cavity 13 to arise relative to the opposing surface 8, with the distance 7 from the base of the cavity to the opposing surface 8 determining the thickness of the cement layer.

Figure 2:
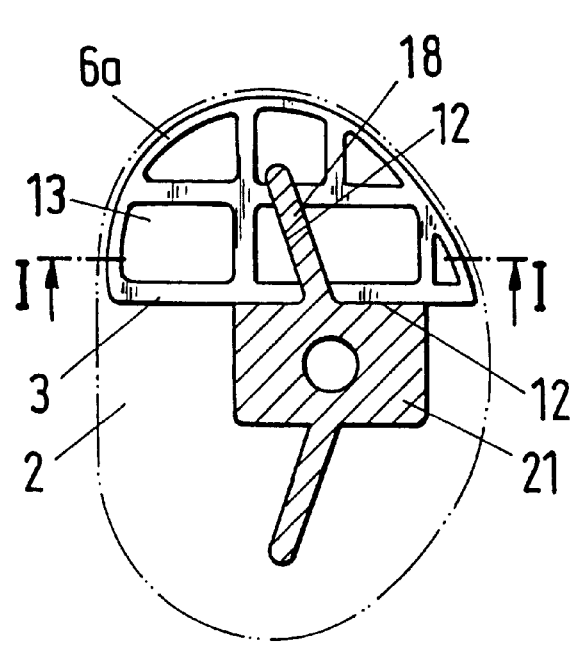
FIG. 2 is a schematic view showing the centering of a spacer in accordance with FIG. 1 in a plan view.

Several cavities 13 of this kind with a peripherally extending edge 6a are shown in FIG. 2. A portion of the outer contour of the spacer 3 and an incision 19 form auxiliary surfaces 12, by means of which the spacer is centered at a rib 18 and at a shaft 21 of the platform 1.

Figure 3A:
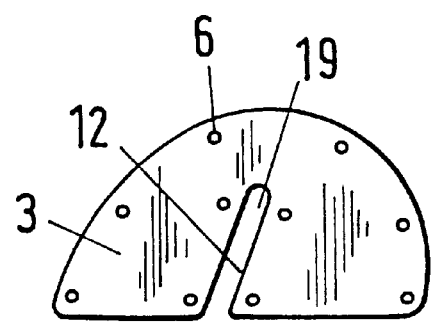
FIG. 3a is a schematic view of the areal face of a spacer in accordance with FIG. 1 with protruding knobs.

FIGS. 3a and 3b show a spacer 3 with protruding knobs 6 which determine the thickness of the bone cement when an opposing surface is pressed against it and the excess cement is pressed out sideways.

FIGS. 4a, 4b and 4c show spacers 3 for condyles of an artificial hip joint which can be cemented to the femur bone, with the interposition being made distally in FIG. 4a and towards the posterior in FIG. 4b. The securing surfaces 10a, 11a on the prosthesis part 1 are provided with a structure 14 in such a manner that an engagement with the bone cement can take place. The spacers 3 are provided as in FIG. 4c with a peripherally protruding edge 6a facing the prosthesis in order to determine the thickness of the cement layer. Centering pins 20 which project beyond the peripherally extending edge 6a are placed in the vicinity of the corners and have protruding cylindrical auxiliary surfaces 12 which can be inserted into bores in the prosthesis in order to center the spacer there. The surfaces 10, 11 at the spacer and the opposing surfaces 10a, 11a at the prosthesis part are each planar. The thickness 9 of the spacer is determined by the protrusions 6a lying in contact at the end faces, in relation to which the depth of the cavities 13 is also determined.

FIG. 5a shows an angled constructional form for a spacer 3 which corresponds to a combination of the contours in FIGS. 4a and 4b. FIGS. 5b, 5c show a spacer 3 typical for this arrangement. The angled spacer 3 has a peripherally extending edge 6a towards the bone at each limb and a lower base lying lower than it at a distance 7 by which a cavity 13 for receiving the bone cement is formed. Rounded pins 20a, b, c are attached in each case at the side facing the prosthesis, each of which has a protruding shoulder 6b at its foot with a height that determines the thickness of the cement layer up to the prosthesis. A cylindrical guide surface of the lowermost pin 20a is inserted first into a counterbore of the prosthesis after application of the cement to the prosthesis, while the remaining pins 20b and 20c, which are located on an inclined transition surface and on a surface set at an angle of 90°, project only with a slight rounding over the shoulders 6b and can thus snap into counterbores of the prosthesis within the scope of the elasticity of the spacer 3. In this manner the spacer itself can be steered with the prosthesis up to the prosthesis via the pins 20a, b, c while the cement is still fluid.

Figure 6:
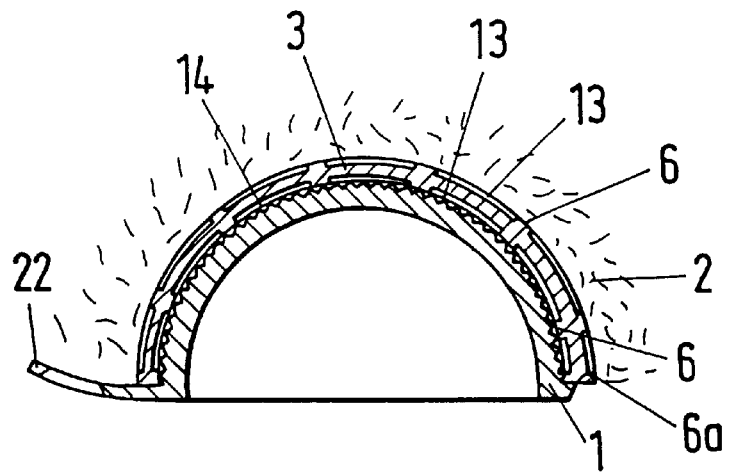
FIG. 6 is a schematic section through a metallic hip joint shell cemented into place with a shell-shaped spacer.
Figure 7:
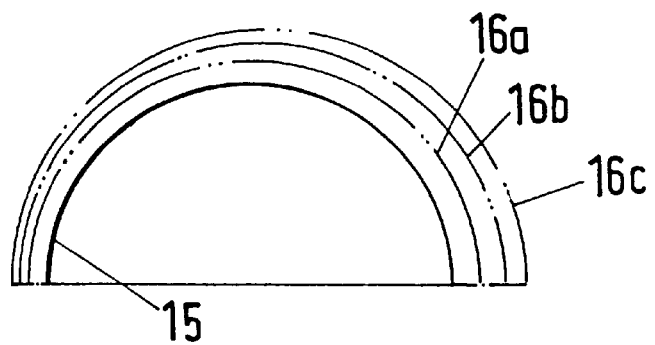
FIG. 7 is a schematic illustration of the eccentric variation of the outer surface for shell-shaped spacers in accordance with FIG. 6 with the same inner surface.
Figure 8:
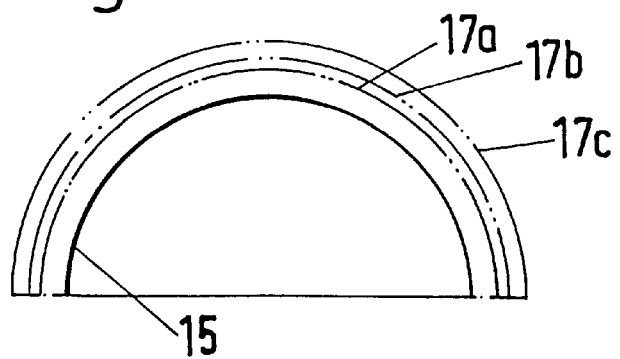
FIG. 8 is the schematic illustration of the concentric variation of the outer surface for shell-shaped spacers in accordance with FIG. 6 with the same inner surface.

This technique for changing the spacing of functional surfaces on cemented prosthesis parts can also be used for cemented hip joint shells. FIG. 6 shows a metallic hip joint shell 1 which has a structured outer surface 14 for the engagement with the bone cement. An outer shell 3 that is prefabricated of bone cement has protrusions 6 on its inner face and on its outer face which can also be present in the form of peripherally extending edges 6a for squeezing out fluid cement in order to form bounded cavities for fluid bone cement. The cement combines with the spacer 3 to form a homogeneous piece, while it is forced in the usual manner into engagement with the bone 2 and with the prosthesis 1. The spacer in the form of an additional shell has an inner surface defined by the protrusions 6, 6a and, in accordance with FIG. 7, non-concentric outer surfaces 16a, b, c at correspondingly differing distances likewise defined by protrusions 6, 6a. With the non-concentric outer surfaces, an additional displacement of the inner shell 3 transverse to its polar axis is possible, whereas for a concentric arrangement in accordance with FIG. 8, different outer surfaces 17a, b, c permit only a displacement in the direction of the polar axis of the inner shell 3. In addition, securing lugs 22 can be formed on the inner shell and can be anchored, for example by means of screws, in the bone.

We claim:

1. A kit system for cemented prostheses in which a prosthesis part is adapted to be fastened to a resected bone with liquid bone cement, the kit comprising at least one prefabricated spacer of hardened bone cement which is hardened from said liquid bone cement, the spacer having a pair of faces, said spacer being secured at said pair of faces respectively to opposing surfaces of respectively the resected bone and said prosthesis part with said liquid bone cement to increase a distance between said prosthesis part and the resected bone, said spacer including at least 1 protrusion on at least one face of said pair of faces which determine a minimum distance between the other face to the corresponding opposing surface.

2. A kit system in accordance with claim 1 including a plurality of spacers having differing thicknesses for said prosthesis part.

3. A kit system in accordance with claim 2 wherein said faces of said spacers are parallel to one another.

4. A kit system in accordance with claim 2 wherein said faces of said spacers are oriented in a wedge-like manner to one another.

5. A kit system in accordance with claim 2 wherein said spacers are angled off in a plurality of planes in order to be able to lie in contact with opposing surfaces which are angled off in a plurality of planes.

6. A kit system in accordance with claim 1 wherein said at least one protrusion is formed on said spacer as peripherally extending edges in order to squeeze out said liquid bone cement against the opposing surface and in order to enclose said liquid bone cement in a cavity relative to the opposing surface.

7. A kit system in accordance with claim 6 wherein said cavity is substantially planar.

8. A kit system in accordance with claim 1 wherein said spacer can be centered with said prosthesis part by auxiliary surfaces provided in said spacer for cooperating with said prosthesis part.

9. A kit system in accordance with claim 1 wherein the spacer includes protrusions on both faces.

* * * * *